(12) United States Patent
Walker (10) Patent No.: US 11,383,236 B2
(45) Date of Patent: Jul. 12, 2022

(54) POLYMERASE CHAIN REACTION USING A MICROFLUIDIC CHIP FABRICATED WITH PRINTED CIRCUIT BOARD TECHNIQUES

(71) Applicant: Christopher Walker, Palo Alto, CA (US)

(72) Inventor: Christopher Walker, Palo Alto, CA (US)

(*) Notice: Subject to any disclaimer, the term of this patent is extended or adjusted under 35 U.S.C. 154(b) by 567 days.

(21) Appl. No.: 16/188,251

(22) Filed: Nov. 12, 2018

(65) Prior Publication Data

US 2019/0143323 A1 May 16, 2019

Related U.S. Application Data

(60) Provisional application No. 62/584,122, filed on Nov. 10, 2017.

(51) Int. Cl.
*B01L 3/00* (2006.01)
*B01L 7/00* (2006.01)
*C12Q 1/686* (2018.01)

(52) U.S. Cl.
CPC ... *B01L 3/502715* (2013.01); *B01L 3/502738* (2013.01); *B01L 7/52* (2013.01);
(Continued)

(58) Field of Classification Search
None
See application file for complete search history.

(56) References Cited

U.S. PATENT DOCUMENTS 3,945,618 A 3/1976 Shoh
6,132,580 A * 10/2000 Mathies .............. B01J 19/0093
204/453
(Continued)

FOREIGN PATENT DOCUMENTS

CA 2379130 A1 1/2001
DE 10041823 C2 3/2002
(Continued)

OTHER PUBLICATIONS

Jung et al. "Recent Improvement in Miniaturization and Integration of A DNA Analysis System for Rapid Forensic Analysis (MiDAS)", Journal of Forensic Investigation, vol. 2 (Aug. 2014), Issue 2, pp. 1-7. (Year: 2014).*
(Continued)

*Primary Examiner* — William H. Beisner
(74) *Attorney, Agent, or Firm* — Wei & Sleman LLP (57) ABSTRACT

Techniques are provided for a microfluidic chip for performing a microfluidic reaction. The microfluidic chip includes a rigid layer, a first polymer layer that forms a first surface of a microfluidic chamber within the microfluidic chip, a first adhesive layer disposed between the rigid layer and the first polymer layer, and a second polymer layer that forms a second surface of the microfluidic chamber, and a first port connecting an exterior of the microfluidic chip to the microfluidic chamber through at least the rigid layer, the first polymer layer, and the first adhesive layer. A first self-sealing valve is formed in the first polymer layer and disposed within the first port, the first self-sealing valve configured to seal directly against the rigid layer through a first gap in the first adhesive layer in response to pressure from thermal expansion of a fluid within the microfluidic chamber.

9 Claims, 9 Drawing Sheets

(52) U.S. Cl.
CPC ..... *B01L 2200/04* (2013.01); *B01L 2200/147* (2013.01); *B01L 2300/0816* (2013.01); *B01L 2300/1827* (2013.01); *B01L 2300/1894* (2013.01); *C12Q 1/686* (2013.01)

(56) References Cited

U.S. PATENT DOCUMENTS

| | | |
|---|---|---|
| 6,403,037 B1 | 6/2002 | Chang et al. |
| 6,443,179 B1 | 9/2002 | Benavides et al. |
| 6,447,727 B1 | 9/2002 | Parce et al. |
| 6,572,830 B1 | 6/2003 | Burdon et al. |
| 6,586,233 B2 | 7/2003 | Benett et al. |
| 6,613,560 B1 * | 9/2003 | Tso ................. B01L 3/5027 435/287.2 |
| 6,706,519 B1 | 3/2004 | Kellogg et al. |
| 7,863,035 B2 | 1/2011 | Clemens et al. |
| 8,043,950 B2 | 10/2011 | Yamaguchi et al. |
| 8,048,628 B2 | 11/2011 | Pollack et al. |
| 8,088,616 B2 | 1/2012 | Handique |
| 8,124,033 B2 | 2/2012 | Neuzil et al. |
| 8,414,785 B2 | 4/2013 | Walker et al. |
| 9,238,833 B2 | 1/2016 | Chen et al. |
| 9,533,308 B2 | 1/2017 | Rajagopal et al. |
| 10,376,892 B2 | 8/2019 | Rajagopal et al. |
| 2002/0168278 A1 * | 11/2002 | Jeon ................. F16K 99/0034 417/559 |
| 2003/0064507 A1 | 4/2003 | Gallagher |
| 2005/0009101 A1 | 1/2005 | Blackburn |
| 2007/0026426 A1 | 2/2007 | Fuernkranz et al. |
| 2008/0038163 A1 | 2/2008 | Boege et al. |
| 2011/0312841 A1 * | 12/2011 | Silverbrook ...... B01L 3/502707 506/40 |
| 2012/0264202 A1 | 10/2012 | Walker |

FOREIGN PATENT DOCUMENTS

| | | |
|---|---|---|
| DE | 10246283 B3 | 3/2004 |
| EP | 1878502 A1 | 1/2008 |
| JP | 5178528 B2 | 6/2009 |
| KR | 100771862 B1 | 2/2007 |
| WO | WO2004029241 A1 | 4/2004 |

OTHER PUBLICATIONS

Duffy, D., et al., Rapid prototyping of microfluidic systems in poly(dimethylsiloxane), Analytical Chemistry 1998, 70: 4974-4984.

Metz, S., et al., Polyimide-based microfluidic devices, Lab on a Chip 2001, 1: 29-34.

Shen et al., A microchip-based PCR device using flexible printed circuit technology (Sensors and Actuators B 105 (2005) 251-258.

Unger, M., et al., Monolithic microfabricated valves and pumps by multilayer soft lithography, Science 2000, 288: 113-116.

Wego, A., et al., Fluidic microsystems based on printed circuit board technology, Journal of Micromechanical and Microengineering 2001, 11: 528-531.

* cited by examiner

POLYMERASE CHAIN REACTION USING A MICROFLUIDIC CHIP FABRICATED WITH PRINTED CIRCUIT BOARD TECHNIQUES

CROSS-REFERENCE TO RELATED APPLICATIONS

This application claims the benefit of Provisional Application Ser. No. 62/584,122, filed Nov. 10, 2018, the entire contents of which are hereby incorporated by reference as if fully set forth herein, under 35 U.S.C. § 119(e).

FIELD OF THE DISCLOSURE

The present disclosure generally relates to polymerase chain reaction, and relates more specifically to polymerase chain reaction using a microfluidic chip fabricated with printed circuit board techniques.

BACKGROUND

The approaches described in this section are approaches that could be pursued, but not necessarily approaches that have been previously conceived or pursued. Therefore, unless otherwise indicated, it should not be assumed that any of the approaches described in this section qualify as prior art merely by virtue of their inclusion in this section.

The polymerase chain reaction (PCR) is a biochemical technique for duplicating targeted sequences of deoxyribonucleic acid (DNA). In its simplest form, PCR takes an aqueous solution composed of the target DNA sequence, engineered matching sequences (primers), polymerase (an enzyme which assembles DNA from its component bases), and free nucleotides (DNA bases). Above a sequence-specific temperature, DNA denatures ("melts"), and unwinds into two strands. Below a primer-specific temperature, the primers will bind to the DNA strands ("anneal").

The polymerase can attach to the primer-target structure, and, at a polymerase-specific temperature, extend the sequence by binding free nucleotides (the "extension" phase). This results in a copy of the initial DNA sequence. By repeatedly cycling a PCR solution through the three temperatures (melt, anneal, and extension), a trace amount of DNA can be magnified to a detectable quantity. A reaction typically requires between 25 and 35 cycles.

A typical PCR reaction uses only a small quantity (tens to hundreds of microliters) of solution, usually contained in a small, sealed tube, and mounted in a large, temperature controlled block. Each stage of the biochemical reaction does require time to complete; however, the main source of delay is the time required to accurately set the temperature of the block and for the solution to attain thermal equilibrium.

SUMMARY

The appended claims may serve as a summary of the invention.

While each of the drawing figures illustrates a particular embodiment for purposes of illustrating a clear example, other embodiments may omit, add to, reorder, or modify any of the elements shown in the drawing figures. For purposes of illustrating clear examples, one or more figures may be described with reference to one or more other figures, but using the particular arrangement illustrated in the one or more other figures is not required in other embodiments.

DETAILED DESCRIPTION

In the following description, for the purpose of explanation, numerous specific details are set forth in order to provide a thorough understanding of the present invention. It will be apparent, however, that the present invention may be practiced without these specific details. In other instances, well-known structures and devices are shown in block diagram form in order to avoid unnecessarily obscuring the present invention.

It will be further understood that: the term "or" may be inclusive or exclusive unless expressly stated otherwise; the term "set" may comprise zero, one, or two or more elements; the terms "first", "second", "certain", and "particular" are used as naming conventions to distinguish elements from each other does not imply an ordering, timing, or any other characteristic of the referenced items unless otherwise specified; the term "and/or" as used herein refers to and encompasses any and all possible combinations of one or more of the associated listed items; that the terms "comprises" and/or "comprising" specify the presence of stated features, but do not preclude the presence or addition of one or more other features.

General Overview

This document generally describes systems, methods, devices, and other techniques for polymerase chain reaction using a microfluidic chip fabricated with printed circuit board techniques. A microfluidic chip is fabricated with printed circuit board techniques. The microfluidic chip includes a chamber in which a PCR reaction is performed. The microfluidic chip also includes an integrated heater element. By taking advantage of fabrication techniques developed for printed circuit boards, it is possible to inexpensively fabricate a heater element in close contact with the chamber of the microfluidic chip. Since the thermal mass of the chip is minimal, and the heater is tightly thermally coupled to the PCR solution, time lags caused by measurement time constants, and excess thermal mass time constants are eliminated.

Air trapped within the chamber of the microfluidic chip may lead to errors in the PCR reaction. Air may become trapped when the chamber is filled with the PCR solution. Air may also be introduced into the chamber when the temperature is cycled in the chamber during the PCR reaction. Furthermore, when the temperature is cycled, air within the chamber may affect the pressure in the chamber, causing fluid loss and/or additional air introduction. In some embodiments, the chamber designed to prevent air bubbles from becoming trapped during the filling process. In some embodiments, the microfluidic chip includes one or more integrated valve to seal the chamber after filling the chamber with PCR solution.

Precise temperature control and rapid temperature cycling can also increase the accuracy and/or efficiency of the PCR reaction in the microfluidic chip. In some embodiments, in addition to a first heater element, a second heater element is added to the microfluidic chip. For example, a first heater element may be positioned in close contact with a first face of the chamber, and a second heater element may be positioned in close contact with a second face of the chamber. In some embodiments, the microfluidic chip includes electrical connections for measuring the voltage across the heater element/s to accurately determine a temperature at the heater element/s.

A PCR instrument is described herein that electronically couples with the microfluidic chip and causes performance of the PCR reaction within the microfluidic chip. Due to the low power requirements of the microfluidic chip, the PCR instrument can be physically compact and powered by an internal battery. In some embodiments, the PCR instrument includes control electronics that can sense the temperature of the chip and apply power to heat the chamber using by controlling at least one heater element of the microfluidic chip.

Additionally, the PCR instrument may include and control a cooling fan. The PCR instrument may provide a user interface. For example, the PCR instrument may provide a user interface by communicating with a computing device. Additionally, the PCR instrument may include an optical detection system that performs real time detection of sample fluorescence and thus end product DNA detection. Additional features and advantages are apparent from the specification and the drawings.

Microfluidic Chip Overview

Figure 1A:
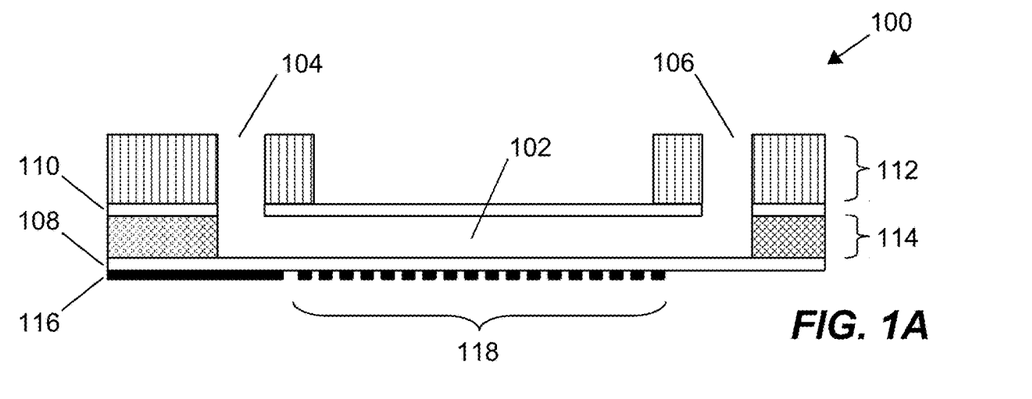
FIG. 1A illustrates a cross section view of a microfluidic chip in an example embodiment.

FIG. 1A illustrates a cross section view of a microfluidic chip in an example embodiment. Microfluidic chip 100 is a fabricated circuit board, such as but not limited to a printed circuit board. In some embodiments, the microfluidic chip 100 is constructed by the lamination of two or more layers of printed circuit board material, such as by pressure, adhesive, resin, curing, temperature, and/or any other method of lamination. The layers may include one or more materials with particular properties, such as conductive values, insulating values, other electrical values, rigidity values, strength values, expansion values, other mechanical values, reactivity, other chemical values, and/or other properties. The microfluidic chip 100 may also include one or more adhesive layers, such as but not limited to acrylate adhesive layers for laminating the layers 108-114. In some embodiments, one or more layers 108-114 are patterned by cutting before alignment and lamination, such as by die cutting, laser cutting, or any other method for cutting.

Voids and patterns may be cut in the material layers before lamination. For example, the microfluidic chamber 102 and the ports 104-106 may be formed by voids in the layers 108-114. In some embodiments, layers 108-110 are made from a polymer film, such as but not limited to polyimide and/or polypropylene. A spacer layer 114 may also be made of polyimide film. In some embodiments, the thickness of the spacer layer 114 defines the height of the microfluidic chamber 102. The microfluidic chip 100 may include one or more rigid layers for structural rigidity.

For example, rigid layer 112 may be a fiberglass reinforced plastic (FR4), layer. The rigid layer 112 allows the microfluidic chip 100 to be handled easily, such as to prevent damage. In some embodiments, the layers 108-114 of the microfluidic chip 100 have a standard thickness that allows the microfluidic chip 100 to be plugged into industry standard edge connectors.

The microfluidic chamber 102 may be a hollow void within the microfluidic chip that receives PCR solution. The microfluidic chamber 102 is filled by injecting the PCR solution into at least one of the ports 104-106. When PCR solution is injected into a first port 104, air is ejected from the other port 106 as the microfluidic chamber 102 is filled. The ports 104-106 may then be sealed, such as by tape, plug, compression to a sealing layer, or another sealing method. Techniques for sealing a microfluidic chamber 102 are described in greater detail hereinafter.

Figure 1B:
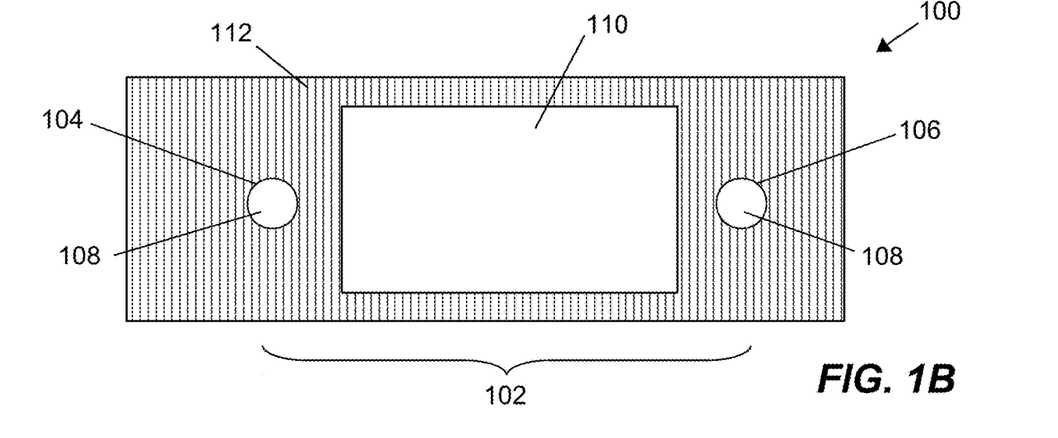
FIG. 1B illustrates a top view of a microfluidic chip in an example embodiment.

FIG. 1B illustrates a top view of a microfluidic chip in an example embodiment. The microfluidic chamber 102 extends between port 104 and port 106. Layer 110 forms the top of the microfluidic chamber 102, and is visible through a void in the rigid layer 112. In some embodiments, the void in the rigid layer 112 allows efficient heating and/or cooling of microfluidic chamber 102 to be performed through layer 110. Layer 108 forms the bottom of the microfluidic chamber 102.

Figure 1C:
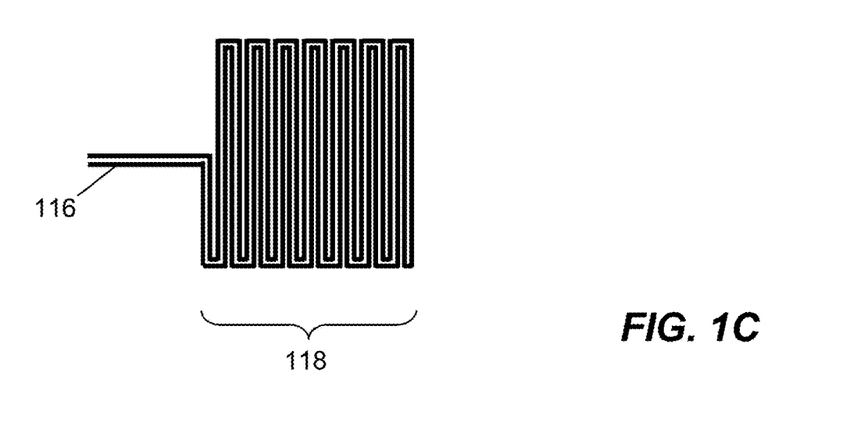
FIG. 1C illustrates an on-chip heater element in an example embodiment.

To perform the PCR reaction, the microfluidic chamber 102 is iteratively heated. For example, the microfluidic chamber 102 may be heated by applying an electrical current to a heater element 118. In some embodiments, the heater element 118 is integrated in a conductive layer 116, such as but not limited to a copper layer. The electrical pattern for the heater element 118 may be defined by photolithography, etching, and/or other printed circuit board fabrication techniques. FIG. 1C illustrates an on-chip heater element in an example embodiment. The heater element 118 is etched in the conductive layer 116. A current may be applied to one or more leads in the conductive layer 116 to activate the heater element 118. The heater element 118 may be in close contact with the microfluidic chamber 102. For example, the heater element 118 may be disposed on a first exterior surface of the microfluidic chamber 102, such as on layer 118.

In some embodiments, the microfluidic chamber 102 is cooled between heating cycles. For example, an external airflow may be directed at the microfluidic chamber 102 to cool the PCR solution contained within. Once the reaction is complete, the PCR solution may be removed from the microfluidic chamber 102 from one of the ports 104-106. The ports 104-106 may be designed to accommodate the external diameter of a pipette or syringe needle for manual filling and/or extraction.

Internal Air Management

When the filling microfluidic chip 100 with the PCR solution, air bubbles may become trapped in the microfluidic chamber 102. Even with the chip sealed after filling, these can expand as the chip is heated, leading to errors in temperature control and increased internal pressure in the system.

Chamber Shape for Minimizing Trapped Air

Figure 2A:
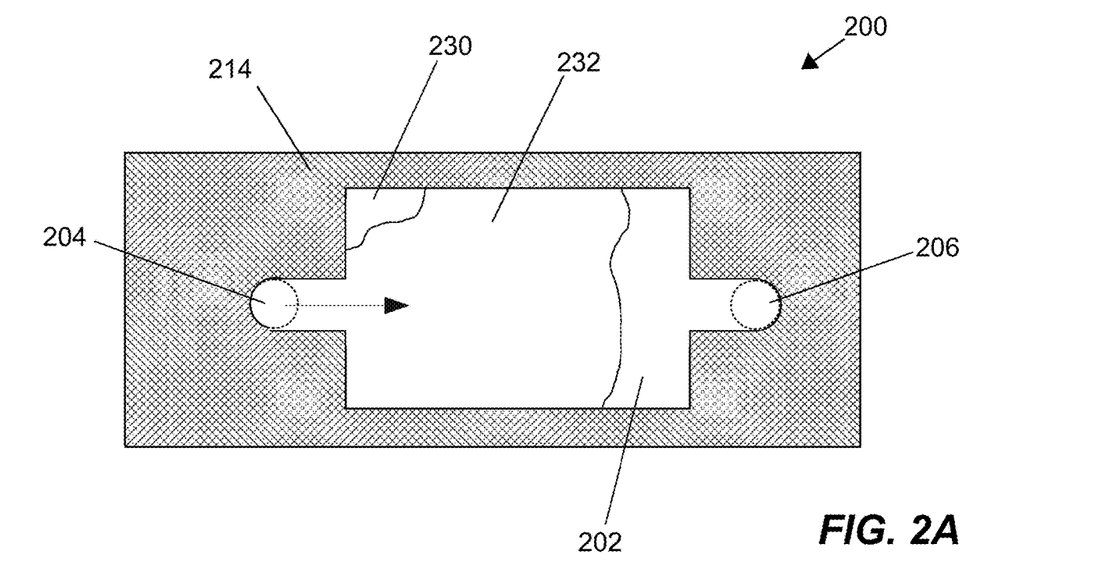
FIG. 2A illustrates a spacer layer with a microfluidic chamber in an example embodiment.

FIG. 2A illustrates a spacer layer with a microfluidic chamber in an example embodiment. The spacer layer 204 of the microfluidic chip 200 includes a void that forms a microfluidic chamber 202. Corners and sharp transitions in the microfluidic chamber 202 geometry make it easier for air, such as air bubble 230, to become trapped within the microfluidic chamber 202 when a fluid 232 is introduced to the microfluidic chamber 202 through a port 204. As the fluid 232 is introduced through port 204, air in the microfluidic chamber 202 is generally ejected from port 206, but the trapped air bubble 230 will not be ejected and will remain in the microfluidic chamber 202.

Figure 2B:
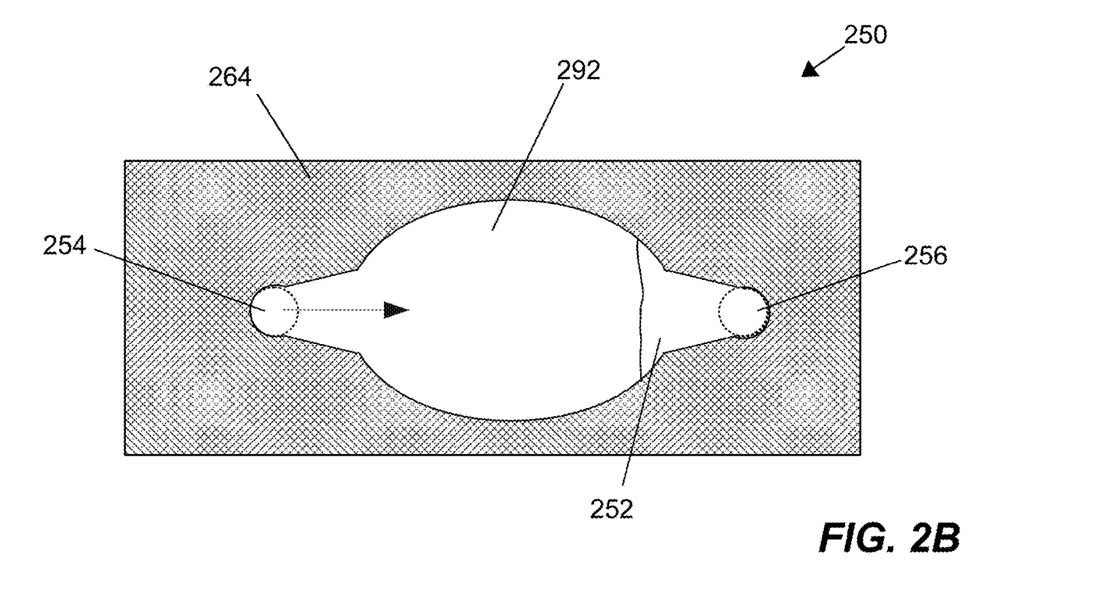
FIG. 2B illustrates a spacer layer with a microfluidic chamber in an example embodiment.

FIG. 2B illustrates a spacer layer with a microfluidic chamber in an example embodiment. The spacer layer 264 of the microfluidic chip 250 includes a void that forms a microfluidic chamber 252. The void of the spacer layer 264 that form the walls of the microfluidic chamber 252 includes smoothed transitions between a first port 254 through which a fluid 292 is introduced and the microfluidic chamber 252. The void of the spacer layer 264 also includes smoothed transitions between the microfluidic chamber 252 and a second port 256 through air is ejected when the fluid 292 is introduced from the first port 254.

In some embodiments, the sidewalls of the microfluidic chamber 252 are configured to reduce the likelihood of air becoming trapped within the microfluidic chamber 252. For example, the microfluidic chamber 252 may have a smoothly curved ellipsoid geometry that greatly reduce the probability of any air bubble becoming trapped when fluid is introduced. Other geometries for the microfluidic chamber 252, such as a rhomboid, a rounded rectangle, and any other shape that eliminates sharp interior corners may also work for the chamber geometry.

Self-Sealing Chamber to Prevent Air Introduction

The ports of a microfluidic chip may be sealed before the microfluidic chamber is thermally cycled. If the ports are left open, expansion and/or contraction of the microfluidic chamber can expel fluid and introduce air bubbles into the PCR solution within the microfluidic chamber. For example, the ports may be sealed with adhesive tape, an external clamp, plugs, or the like.

Figure 3A:
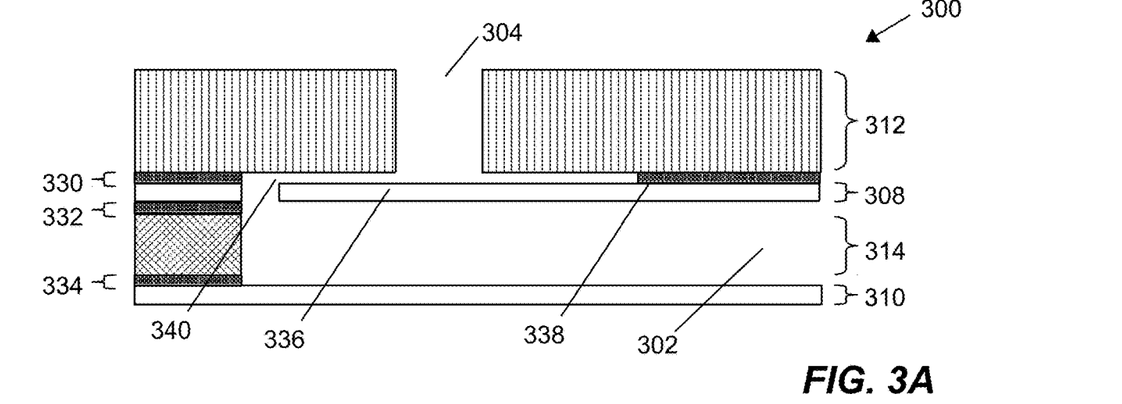
FIG. 3A illustrates an internal valve for a microfluidic chamber in an example embodiment.

In some embodiments, one or more ports of the microfluidic chip include a self-sealing valve. FIG. 3A illustrates an internal valve for a microfluidic chamber in an example embodiment. FIG. 3A shows the self-sealing valve 336 in a neutral position. A microfluidic chip 300 includes a rigid layer 312, polymer layers 308-310, a spacer layer 314, and adhesive layers 330-334. The adhesive layers 330-334 attach layers 308-314. A self-sealing valve 336 is present in the upper polymer layer 308 for a port 304 to the microfluidic chamber 302 formed.

Figure 3B:
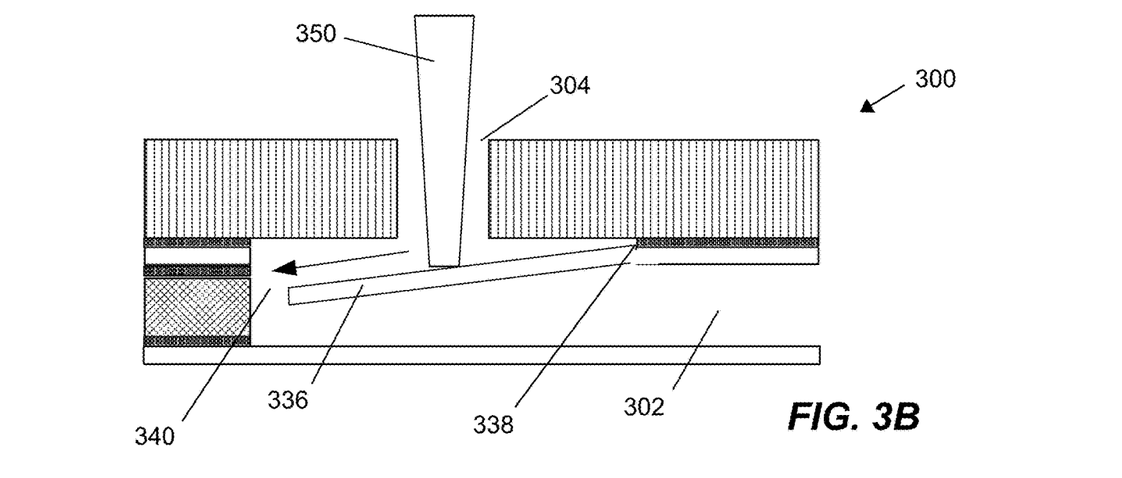
FIG. 3B illustrates filling a microfluidic chamber of an internal valve in an example embodiment.
Figure 3C:
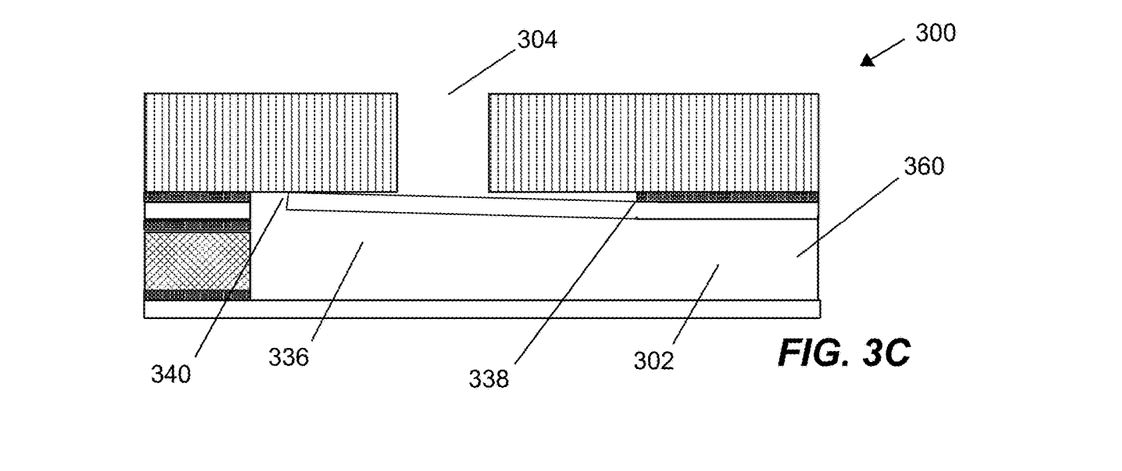
FIG. 3C illustrates self-sealing of an internal valve or a microfluidic chamber in an example embodiment.

In some embodiments, in addition to the void in the spacer layer 314 that forms the microfluidic chamber 302, an additional area is removed around the port 304 in the upper polymer layer 308. The self-sealing valve 336 formed by the polymer layer 308 extends into this area, but the self-sealing valve 336 is not bonded to the rigid layer 312. The adhesive layer edge 338 of adhesive layer 330 does not extend the length of the self-sealing valve 336, allowing the self-sealing valve 336 to move vertically, either into the microfluidic chamber 302 (as shown in FIG. 3B) or up against the rigid layer 312 (as shown in FIG. 3C). That is, a gap around the port 304 in the adhesive layer 330 allows the self-sealing valve 336 to directly seal against the rigid layer 312.

FIG. 3B illustrates filling a microfluidic chamber of an internal valve in an example embodiment. In FIG. 3B, a fluid transfer instrument 350, such as a pipette tip, syringe needle, or other device, is inserted in the fluidic port 304. When the fluid transfer instrument 350 is inserted, the valve 336 is depressed into the open area in the spacer layer 314, the valve opening 340 is widened and the fluid transfer instrument 350 is connected to the microfluidic chamber 302. In this position, PCR solution or another fluid may injected and/or extracted from the microfluidic chamber 302.

FIG. 3C illustrates self-sealing of an internal valve or a microfluidic chamber in an example embodiment. FIG. 3C shows the microfluidic chip 300 after a fluid is introduced into the microfluidic chamber 302. With the fluid transfer instrument 350 removed and the microfluidic chamber 302 under pressure from thermal expansion, the self-sealing valve 336 is forced into contact with the rigid layer 312, closing the valve opening 340 and sealing the microfluidic chamber 302.

Since polyimide bends but does not deform significantly, the quality of the seal of the self-sealing valve 336 will be lower than one formed from an elastomeric material. However, the seal need not be perfect; as long as it is reasonably tight, the thin layer of fluid trapped between the self-sealing valve 336 and the rigid layer 312 will help keep the self-sealing valve 336 closed and prevent major fluid loss and bubble entrainment through the port 304. Alternatively and/or in addition, another material may be used for the upper layer that forms the top of the microfluidic chamber 302.

Additional self-sealing valves may be constructed in a similar manner for one or more other ports of the microfluidic chip 300, including any port for introducing a fluid and/or any port for releasing air that is ejected when a fluid is introduced in the microfluidic chamber 302 of the microfluidic chip 300.

Chamber Heater Elements

Figure 4:
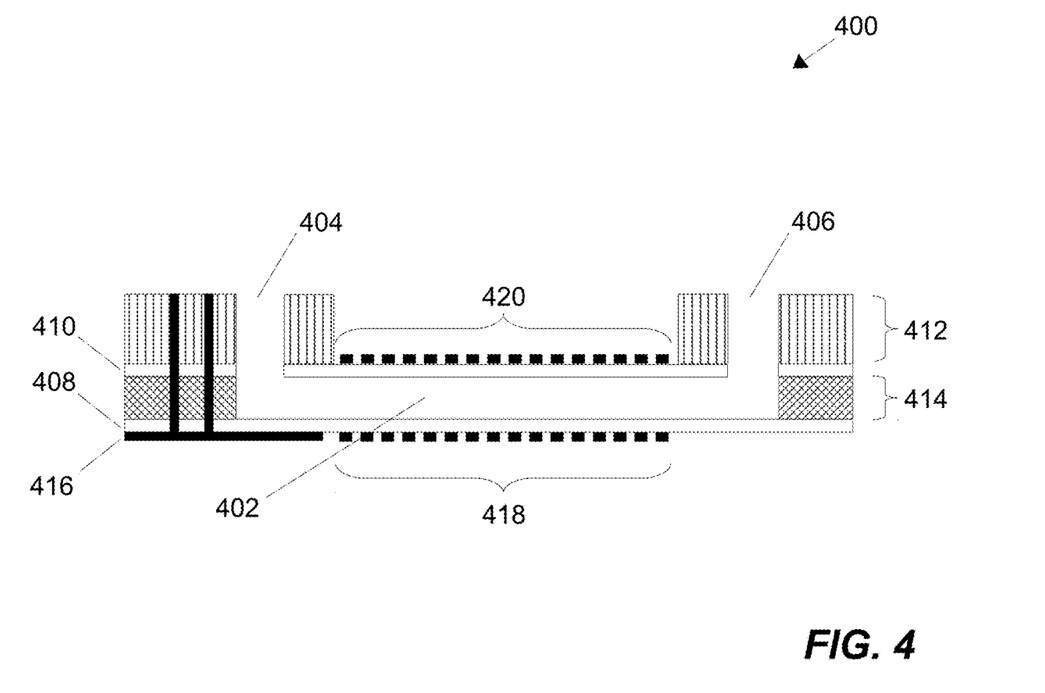
FIG. 4 illustrates a cross section view of a microfluidic chip with a second heater element in an example embodiment.

In some embodiments, a second heater element is added to the microfluidic chip. FIG. 4 illustrates a cross section view of a microfluidic chip with a second heater element in an example embodiment. A microfluidic chip 400 includes a rigid layer 412 and a spacer layer 414 sandwiched between a first polymer layer 408 and a second polymer layer 410. A microfluidic chamber 402 is formed in a void in the spacer layer 414. Ports 404-406 allow for the introduction and removal of PCR solution as well as the ejection of air from the microfluidic chamber 402.

A first heater element 418 and a second heater element 420 are in close contact with the microfluidic chamber 402. For example, the heater element 418 may be disposed on a first exterior surface of the microfluidic chamber 402 on the first polymer layer 408, while a second heater element 420 may be disposed on a second exterior surface of the microfluidic chamber 402 on the second polyamide layer 410. In this configuration, the first heater element 418 and the second heater element 420 are disposed on opposite surfaces of the microfluidic chamber 402. This configuration of two heater elements 418-420 may increase the heating rate, allowing for faster thermal cycling of the microfluidic chamber 402 and the PCR solution contained therein. An example thermal cycling scheme is described in greater detail hereinafter.

Precision Voltage-Sensing for Temperature Control

In some embodiments, the microfluidic chip includes electrical connections for measuring the voltage across the heater element/s to accurately determine a temperature at the heater element/s. This allows for an integrated temperature sensor on the microfluidic chip. The integrated temperature sensor is beneficial to allow for accurate and fast temperature measurements, which can be critical to efficient and/or accurate performance and control of the PCR process. When the temperature sensor is integrated into the layers of the microfluidic chip, the additional cost of the temperature sensor can be greatly reduced.

Figure 5:
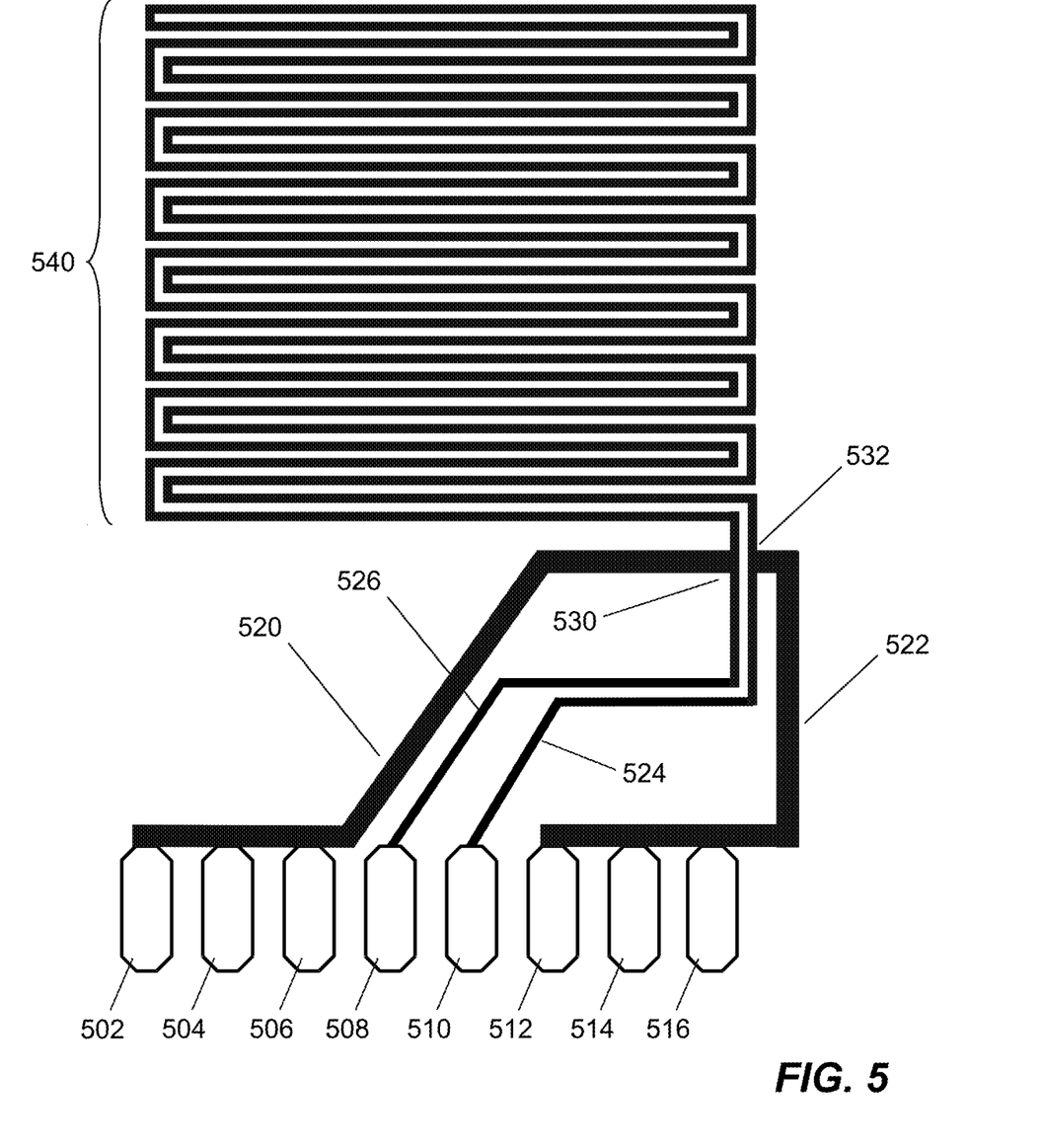
FIG. 5 illustrates an on-board temperature control system with a heater element in an example embodiment.

FIG. 5 illustrates an on-board temperature control system with a heater element in an example embodiment. In a conductive layer, such as a copper layer of a microfluidic chip, a heater element 500 is connected by traces 520-626 to connection pads 502-516 of the microfluidic chip. The connection pads 502-516 allow for powering and control of the heater element 540. For example, the connection pads 502-516 may allow insertion and connection of a microfluidic chip to an external device, such as a PCR instrument.

A drive circuit powers the heater element 540 and includes pads 502-506 and 512-516 and traces 520 and 522. The drive circuit allows a voltage to be applied from an external source to connection pads 502-506 and 512-516 to power the heater element 540. A separate set of traces 524-526 and connection pads 508-510 on the heater layer allow for a precise measurement of the voltage across the heater when a drive current is applied. Combined with a precision measurement of the drive current, and knowledge of the material properties of the heater element 540, the heater element 540 itself may be used to sense the chamber temperature. The separate set of traces 524-526 and connection pads 508-512 form a voltage sensing circuit with minimal current draw. The voltage sensing traces 524-526 connect directly to the heater element 540 at points 530-532, reducing errors caused by voltage drop along the drive traces 520-522 and connection resistance. For example, with a 1 amp drive current, and a connection resistance of 50 milliohms per contact, a 100 millivolt voltage error will accrue across the drive contacts 502-508 and 512-516. However, with a voltage sensing circuit that draws only 0.5 milliamps, and separate traces 524-524 to the heater element 540, the error is reduced to 500 microvolts. Using the heater element 540 in the conductive layer as a temperature sensor lets the PCR instrument effectively measure and control the temperature of the face of the microfluidic chamber with precision.

In some embodiments, temperature sensing of the microfluidic chip is performed by an integrated four-point probe measurement on the microfluidic chip. The on-chip four-point probe connection points allow both current and voltage to be accurately measured simultaneously; this allows the temperature of the resistive heater element to be determined from knowledge of the material properties of the material, thus allowing the heater to also function as a temperature sensing element. In some embodiments, a secondary sensor is used to calibrate the chip temperature relative to the ambient temperature. This sensor is integrated into the instrument, in the path of the cooling airflow to the chip. Optionally, temperature detection by an infrared thermometer sensor (typically a thermopile) may also be used for sensing and calibration.

Example Instrument Architecture

A PCR instrument is described herein that electronically couples with the microfluidic chip and causes performance of the PCR reaction within the microfluidic chip. Due to the low power requirements of the microfluidic chip, the PCR instrument can be physically compact and powered by an internal battery. In some embodiments, the PCR instrument includes control electronics that can sense the temperature of the chip and apply power to heat the chamber using by controlling at least one heater element of the microfluidic chip.

In some embodiments, the PCR instrument includes a case containing control electronics, one or more cooling fans, a power supply, and a computer interface. A microfluidic chip is plugged into an edge connector of the PCR instrument. The cooling fan may direct air at the microfluidic chip, such as by having the chip mounted horizontally directly above the fan, or laterally in a laminar flow system. A laminar flow system, composed of the cooling fan/s and a shroud which partially encloses the microfluidic chip, may provide for faster heat transfer and thus higher cooling rates. The control electronics may be powered either via an external power supply, or an internal battery. In some embodiments, the PCR instrument operates at voltages ranging from 7 VDC to 12 VDC, allowing for 7 cell nickel metal hydride batteries, 2 cell lithium batteries, or common external supplies.

Figure 7:
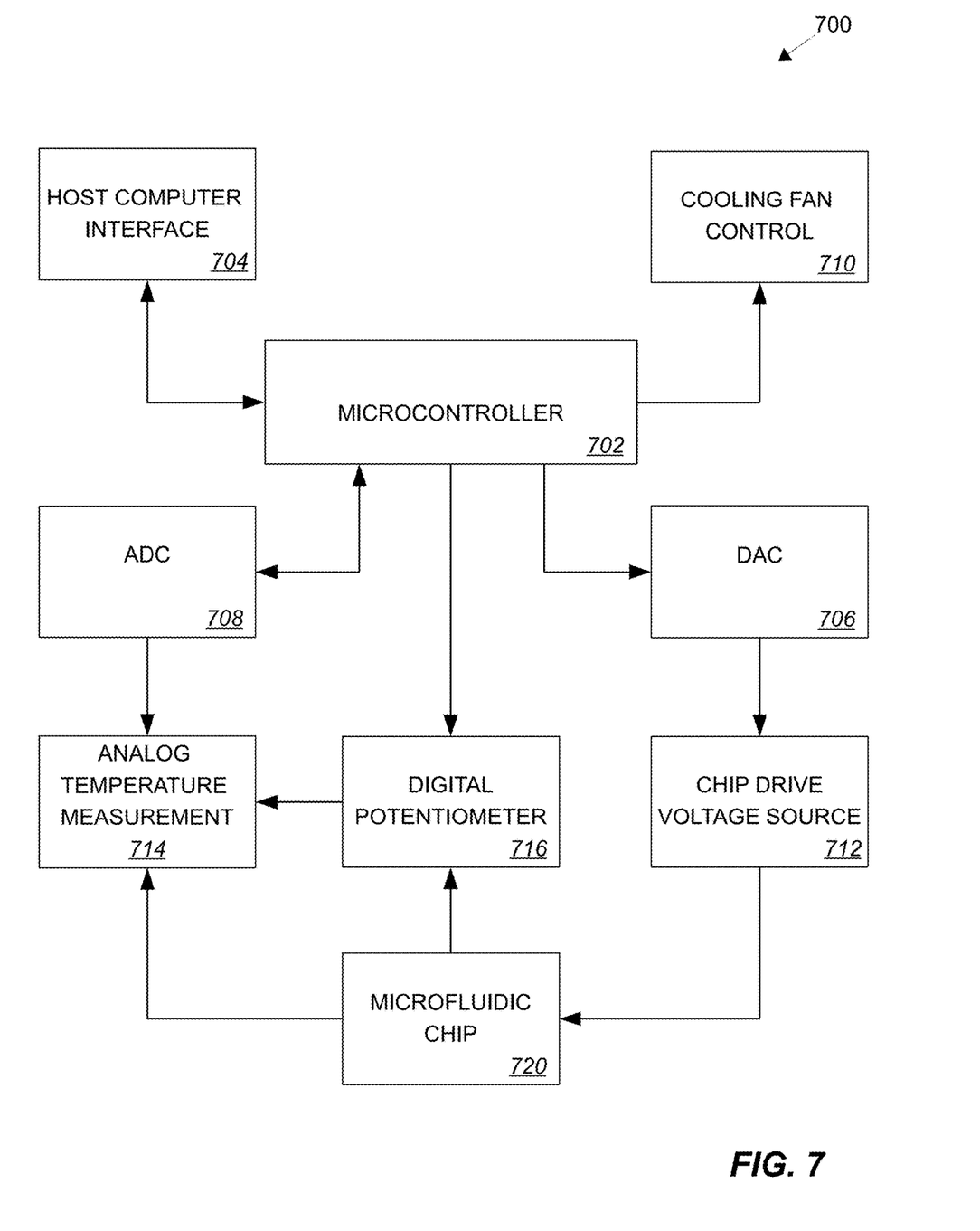
FIG. 7 illustrates a system for performing PCR using a microfluidic chip in an example embodiment.

FIG. 7 illustrates a system for performing PCR using a microfluidic chip in an example embodiment. System 700 may be deployed in an external instrument that electronically couples with the microfluidic chip 720, such as a PCR instrument. A microfluidic chip 720 is powered by a chip drive voltage source 712 controlled by a digital to analog converter (DAC) 706. Sense signals from the microfluidic chip 720 are amplified by an instrument amplifier, filtered to reduce noise, and captured by an analog to digital converter (ADC) 708. The ADC 708 has multiple ports, and is capable of measuring multiple differential voltages. Both the ADC 708 and DAC 706 are connected to a microcontroller 702 via SPI bus.

The microcontroller 702 converts data from the ADC 708 into temperature, and then pulses the DAC 706 output to apply power to the microfluidic chip 720. The microcontroller 702 can thus sense and set the microfluidic chip 720 temperature in a real time feedback loop. By interfacing via SPI bus to a digital potentiometer 716 used in conjunction with the heater element resistor of the microfluidic chip 720 as a Wheatstone bridge, the microcontroller 702 is able to calibrate the sensing process for ambient temperature and chip-to-chip fabrication variance. The microcontroller 702 can set microfluidic chip 702 temperatures, hold times, and cycle the microfluidic chip 720 through a full PCR reaction. In some embodiments, the microcontroller 702 is programmed in an object-oriented paradigm, allowing for code modularity and flexibility.

In some embodiments, the system 700 includes a host computer interface 704. The host computer interface 704 may connect the microcontroller 702 to a computing device, such as a desktop computer, a mobile phone, a smartphone, a tablet, or another computing device, that allows a user to communicate with the microcontroller 702. For example, the host computer interface 704 may communicate with a computing device with a display to provide a user interface accessible by a user. In some embodiments, the host computer interface 704 lets the user set the temperatures, hold times, other instrument parameters, and/or perform calibrations. It can also capture, store and/or display temperature and other telemetry data from the PCR instrument in real time.

Analog Architecture

An externally mounted sensor, such as a bandgap reference or thermistor, may be attached to the microfluidic chip, and the temperature measured through conventional sensing architectures. A better approach is to determine the temperature from the temperature coefficient of resistance (TCR). The TCR defines the change in resistance as a function of the ambient temperature. Most conductive materials (in this case, copper) exhibit a linear shift in resistivity with changes in temperature. By measuring the change in resistance of the chip heater, the temperature may be calculated.

In addition to saving the cost of an external sensing element, the TCR approach also allows for a higher level of accuracy and sensing speed. Since the heater and sensor are the same element, there is no time lag due to thermal resistance between heater and sensor, nor is there an error term due to poor thermal coupling. Since the thermal coefficient of resistance is a material property of the heater material (typically copper), it is unaffected by fabrication tolerances resulting in a variety of heater resistances. However, the TCR change is a small effect, and using it to determine the temperature of the chip requires careful design and calibration.

Example Temperature Sensing Circuit

Figure 6:
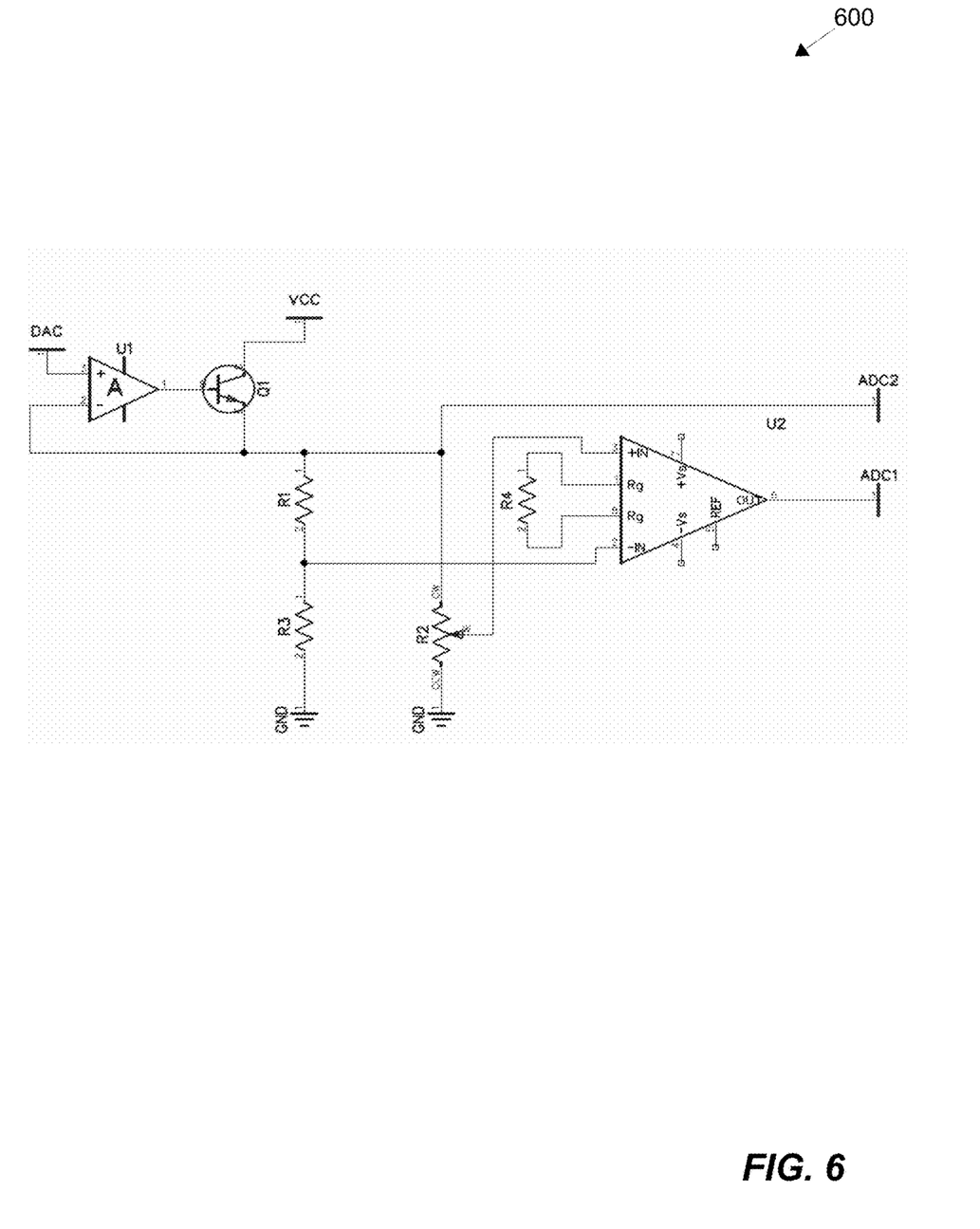
FIG. 6 illustrates a circuit diagram for an on-board temperature control system in an example embodiment.

FIG. 6 illustrates a circuit diagram for an on-board temperature control system in an example embodiment. The on-chip resistive heater (R1) is powered by a voltage source composed of a power transistor (Q1), a series current sense resistor (R3), and an operation amplifier (U1). The transistor, R1, and R3 are in series from the supply voltage to ground as shown. R3 should have a resistance less than, but in the same order of magnitude as R1, have a negligible TCR, and good heat sink characteristics, allowing its temperature to be fairly constant. The output of U1 drives the base of the transistor (or gate, if a FET is used); the negative input of U1 is connected to the emitter (or source, for a FET) of Q1. This forms a feedback loop that holds the emitter of Q1 at the same voltage as the positive input of U1; a controlled voltage can thus be applied to the R1/R3 chain by sending the output of the DAC to U1. The feedback loop shown here is the simplest, but some embodiments may include passive components (resistors, capacitors) to ensure loop stability.

The upper voltage tap from the integrated 4 point probe connection on the microfluidic chip goes directly to an output (ADC2), and the top of a digital potentiometer (R2). The tap from the potentiometer goes to the positive input of an instrument amplifier (U2); the lower voltage tap from the probe connection goes directly to the negative input of U2. The gain of the instrument amplifier is set by a precision resistor R4.

R1, R3, and R2 together form a Wheatstone bridge; the instrument amplifier amplifies the differential voltage across the bridge, and sends it to the output ADC1. As the microfluidic chip heats, the resistance of the heater resistor R1 increases linearly with temperature. With the resistance of R3 constant, the voltage at the negative input of the instrument amplifier will thus drop as the microfluidic chip heats. With the ratio from R2 invariant, the output voltage of the instrument amplifier will thus increase as the microfluidic chip temperature increases.

The outputs ADC1 and ADC2 are connected to the ADC via low pass filters to suppress noise, and buffer amplifiers where appropriate. The microcontroller can then read the voltage values from the ADC via the SPI bus, and compute the temperature.

An example temperature control and temperature cycling scheme is described in reference to FIG. 4. The example scheme includes heater elements 418-420 that are also used for temperature sensing. In a first stage, the microfluidic chamber 402 is below the target temperature for the PCR reaction. The heater elements 418-420 are driven to the maximum allowed by the control circuitry, the temperature of the heater elements 418-420 and the temperature of the microfluidic chamber 402 will increase over time in this state. A second stage of heating begins once the target temperature of the heater elements 418-420 is reached. In the second stage, the heater element 418-420 temperature is held constant by the temperature control system. The microfluidic chamber 402 requires additional time to stabilize in temperature.

The addition of the second heater element 420, when substantially identical to the first heater element 418, doubles the amount of power that can be applied, and about halves the heating time for the PCR solution in the microfluidic chamber 402. The time required for the second stage is determined by the geometry and heat transfer characteristics of the microfluidic chamber 402. For a thin microfluidic chamber 402 (typically 200 microns thick or less), convection processes may be neglected, and heat may be modeled purely by the heat flow equations for a solid material, such as the polyimide layers 410-408 between the heater elements 418-420 and the fluid within the microfluidic chamber 402. The under these conditions, the time required for equilibrium to occur goes roughly as the square of the characteristic distance from the heater elements 418-420 to the opposite side of the chamber—the chamber thickness. With heater elements 418-420 on both faces of the chamber, the characteristic distance is halved; the equalization time delay is thus cut by a factor of 4. Thus, by adding a second heater element 420, the total time required to heat the chamber may be reduced by a factor of ranging from 2 to 4.

Temperature Sensing Digital Self Calibration

Calibration steps may be implemented to ensure accuracy of the temperature sensing circuit. Both the ADC and DAC use a common reference voltage to scale their inputs/outputs. This is provided by a low noise bandgap-referred reference; this reference output voltage is measured separately, and the value stored in the microcontroller. Since the TCR temperature sensing approach is ratiometric, errors in the reference voltage (Vref) are cancelled out.

The gain of the instrument amplifier must be known accurately. This can be set by using a high precision resistor, but a more accurate approach is to measure it directly. Referring to FIG. 6, the DAC, ADC1, and instrument amplifier ports may be reconfigured as follows:

1) The ADC2 port is disconnected from R1 and connected directly to the DAC port via a jumper;

2) The negative input of the instrument amplifier U2 is disconnected from the R1-R3 junction, and connected to ground via a jumper;

3) The positive input of U2 is disconnected from R2, and connected to ADC2 via jumper.

In this configuration, the ADC can capture the output of the DAC directly, and the same output multiplied by the gain of the instrument amplifier U2. The DAC is then swept from 0 to Vref/G, where Vref is the common reference voltage of the DAC and ADC, and G is the nominal gain of the instrument amplifier. The resulting data is captured by the ADC, and used in a linear regression to determine the precise value of the instrument amplifier's gain. By using the ADC to measure both voltages, all systematic errors in the system (DAC nonlinearity, errors in the reference voltage) except for nonlinearity in the ADC are automatically compensated. The precise gain value can then be stored in the microprocessor.

Alternatively, rather than using jumpers to manually reconfigure the circuit, electronic signal switching may be used. This adds additional complexity to the circuit, since the analog signals must now be routed through a multiplexer schema, but would allow for automatic self-calibration implemented in the microcontroller.

The above calibrations need only be required once in the lifetime of the instrument, since they measure fixed characteristics of the control electronics. There are two calibrations that must be performed for each new chip. These are performed automatically via the microcontroller.

With a chip mounted in the instrument, the exact value of the integrated heater resistor must be determined. The calibration process is as follows:

1) The fan is turned on to hold the chip at ambient temperature.
2) The DAC is briefly pulsed at a low control voltage, and the output of the instrument amplifier captured.
3) If the Wheatstone bridge is perfectly balanced, the output of the instrument amplifier should be zero volts. If the output of the instrument amplifier is too high or low, this indicates that the Wheatstone bridge is unbalanced. The ratio of the digital pot is then altered by the microcontroller to balance the Wheatstone bridge.
4) This process is iteratively continued, with a low duty cycle to prevent chip heating, while gradually increasing the DAC voltage until the final drive voltage is realized. When complete, the Wheatstone bridge should be close to balanced at ambient temperature.

Once the Wheatstone bridge is balanced, a final calibration to correct for ambient temperature is performed. An externally mounted temperature sensor may be mounted between the cooling fan and the chip. For example, the temperature sensor may be a bandgap temperature sensor, precision thermistor, linearized active thermistor, thermocouple, or any other device that can function as a temperature sensor. With the fan on, the sensor and chip are forced to the same (ambient) temperature. The DAC is then briefly pulsed at the full drive voltage, the drive and instrument amplifier voltages captured, and the voltage from the bandgap sensor captured as well.

The temperature may now be computed via the thermal coefficient of resistance method for the heater as follows:

$$T_h = \left(\frac{1}{\alpha}\right)\left(\frac{\frac{1}{\gamma - \frac{V_i}{GV_d}} - 1}{\frac{1}{\gamma - \frac{V_{i_a}}{GV_{d_a}}} - 1}\right) + T_a$$

$T_h$ refers to the heater temperature;
$T_a$ is the ambient temperature measured by an external sensor;
$\gamma$ is the resistance ratio of the digital potentiometer;
$V_i$ and $V_d$ are the voltages at the heater drive and instrument amp output;
G is the instrument amplifier gain;
$\alpha$ is the thermal coefficient of resistance of the heater material (e.g. copper); and
the subscript "a" denotes the value captured at ambient temperature during calibration.

Note that this is an almost entirely ratiometric measurement. The absolute values of the heater resistor, sense resistor, and potentiometer are not required to be known accurately. Absolute accuracy in the measurement of the drive and sense voltages is not required either, as long as there are no nonlinearities in the sensing process. This eliminates multiple error sources from the system, and allows for loose fabrication tolerances on the chip heater.

The bandgap sensor may be replaced, or augmented by a thermopile (infrared thermometer) sensor which measures the temperature of the chip. With the top of the chip in the field of view, and the chip held at a steady state temperature, temperature data may be read from this sensor. This approach may replace the ambient measurement via bandgap sensor. Moreover, by taking temperature data at several temperatures, held at steady state, a temperature comparison curve between the resistivity and infrared data may be obtained. This curve can then be used to calibrate the resistivity measurement. This allows for residual inaccuracies in the resistivity measurement to be eliminated, while still providing the benefit of lag free, instant temperature measurement from the resistivity approach.

Cooling Assembly

Figure 8A:
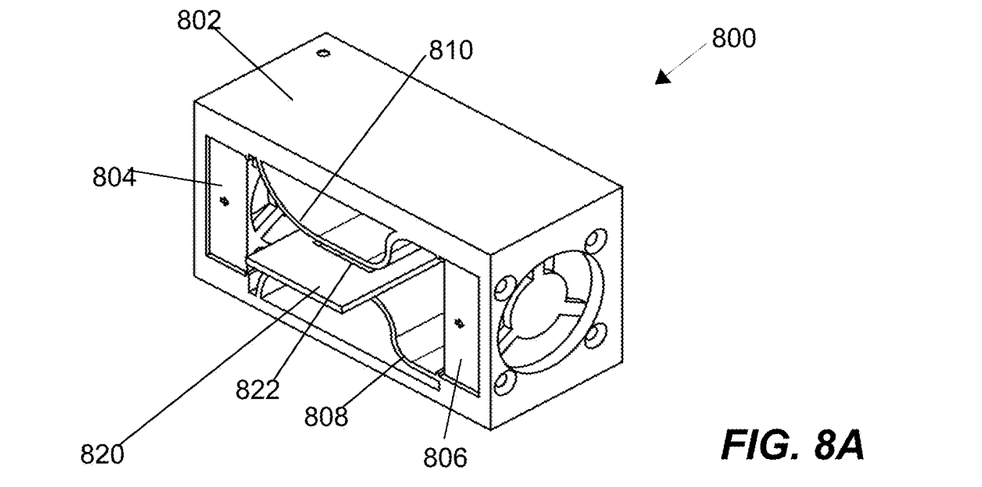
FIG. 8A illustrates a perspective view of a cooling assembly for performing PCR using a microfluidic chip in an example embodiment.

In some embodiments, a cooling assembly is used to quickly lower the temperature of the PCR solution in a microfluidic chamber of a microfluidic chip. The cooling assembly helps rapidly cycle the PCR solution through iterative heating and cooling cycles. FIG. 8A illustrates a perspective view of a cooling assembly for performing PCR using a microfluidic chip in an example embodiment. The cooling assembly 800 includes a housing 802.

Figure 8B:
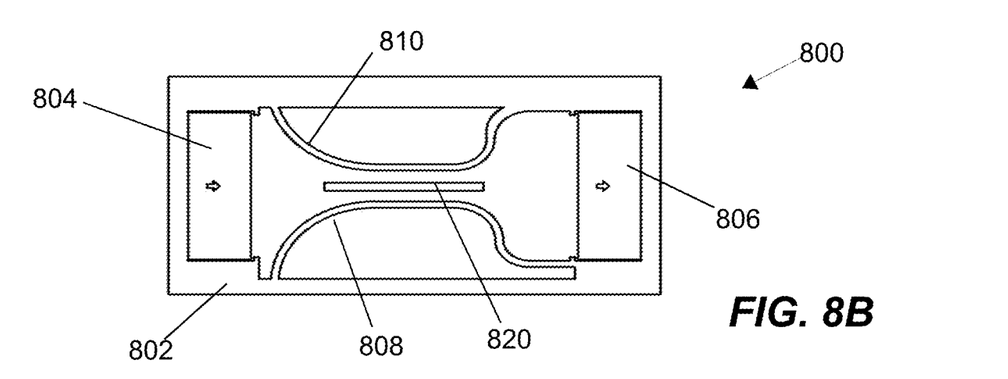
FIG. 8B illustrates a side view of a cooling assembly for performing PCR using a microfluidic chip in an example embodiment.

In some embodiments, the cooling assembly 800 includes at least one fan and laminar flow ducting that shrouds and/or partially encloses the chip. The laminar flow ducting can provide for faster heat transfer and higher cooling rates. For example, an intake fan 804 and an exhaust fan 806 may be mounted to the housing 802 of the cooling assembly 800. When the cooling assembly 800 is in position relative to a microfluidic chip 820, the intake fan 804 and exhaust fan 806 direct an airflow over a microfluidic chamber 822 of the microfluidic chip 820. In some embodiments, the cooling assembly 800 includes laminar flow ducting 808-810 to channel the airflow. The laminar flow ducting 808-810 may be attached to and/or integrated with the housing 802 of the cooling assembly 810. In some embodiments, the laminar flow ducting 808-810 cause a narrowing of the airflow in the plane of the microfluidic chip 820 to maximize heat exchange between the airflow and the surface of the microfluidic chamber 822. FIG. 8B illustrates a side view of a cooling assembly for performing PCR using a microfluidic chip in an example embodiment.

Figure 8C:
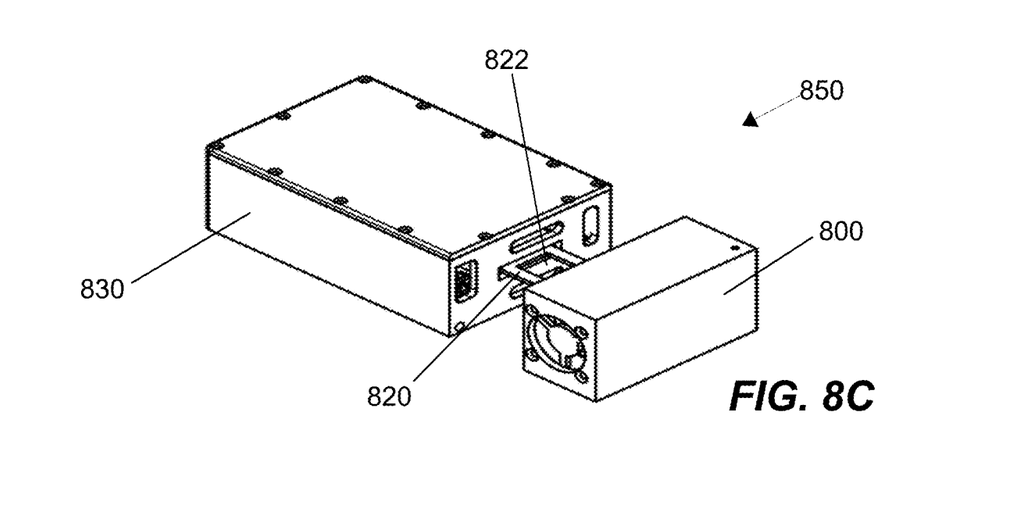
FIG. 8C illustrates a perspective view of a system that includes a PCR instrument and a cooling assembly for performing PCR using a microfluidic chip in an example embodiment.

FIG. 8C illustrates a perspective view of a system that includes a PCR instrument and a cooling assembly for performing PCR using a microfluidic chip in an example embodiment. For example, the system 850 may include one or more components shown in FIG. 7 with respect to system 700. The system 850 includes a PCR instrument 830. The PCR instrument 830 is configured to couple with the microfluidic chip 820 to control a PCR reaction in the microfluidic chamber 822 of the microfluidic chip 820. The system 850 may also couple with the air cooling system 800 so that a microfluidic chip 820 inserted into the PCR instrument 830 is positioned within the cooling assembly 820 as described in FIGS. 8A-B. The PCR instrument 830 may include a microcontroller that is communicatively coupled with the intake fan 804 and the exhaust fan 806 such that the microcontroller can control the cooling of the microfluidic chamber 822 of the microfluidic chip 820.

Figure 9:
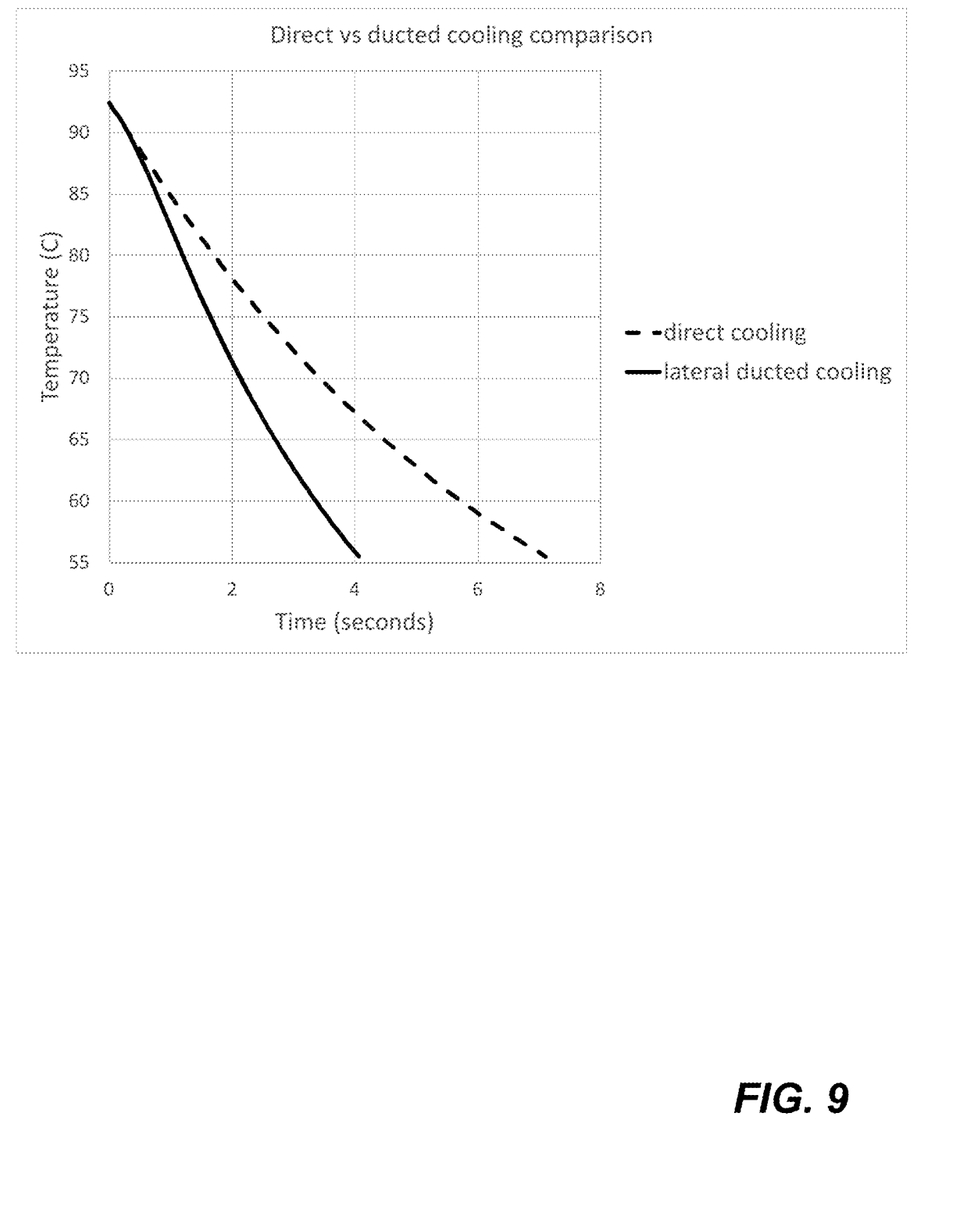
FIG. 9 illustrates a graph comparing performance of a cooling assembly for performing PCR using a microfluidic chip in an example embodiment.

FIG. 9 illustrates a graph comparing performance of a cooling assembly for performing PCR using a microfluidic chip in an example embodiment. The temperature of a microfluidic chip over time, as measured using TCR techniques, is shown using a cooling assembly 800 with laminar flow ducting 808-810 as compared to a single-fan direct cooling assembly. After a PCR solution is stabilized at approximately 92° C. for a holding time in the microfluidic chamber 822, the PCR solution is cooled using the respective cooling assembly. The cooling time to 55° C. is drastically reduced by using the cooling assembly 800 with laminar flow ducting 808-810.

Other Aspects of Disclosure

In the foregoing specification, embodiments of the invention have been described with reference to numerous specific details that may vary from implementation to implementation. The specification and drawings are, accordingly, to be regarded in an illustrative rather than a restrictive sense. The sole and exclusive indicator of the scope of the invention, and what is intended by the applicants to be the scope of the invention, is the literal and equivalent scope of the set of claims that issue from this application, in the specific form in which such claims issue, including any subsequent correction.

What is claimed is:

1. A microfluidic chip for performing a microfluidic reaction comprising:
   a rigid layer comprising a first void in the rigid layer that forms a portion of a first port;
   a first polymer layer that forms a first surface of a microfluidic chamber in which the microfluidic reaction is performed within the microfluidic chip, the first polymer layer comprising a first self-sealing valve portion of the first polymer layer positioned adjacent to the first void of the rigid layer;
   a first adhesive layer disposed between the rigid layer and the first polymer layer that bonds the first polymer layer to the rigid layer, wherein the first adhesive layer does not extend over a length of the first self-sealing valve portion to allow movement of the first self-sealing valve portion;
   a second polymer layer that forms a second surface of the microfluidic chamber; and
   wherein the first port connects an exterior of the microfluidic chip to the microfluidic chamber through the first self-sealing valve portion of the first polymer layer;
   wherein the first self-sealing valve portion of the first polymer layer depresses into the microfluidic chamber in response to pressure applied by a fluid transfer instrument inserted into the first void;
   wherein the first self-sealing valve portion of the first polymer layer is configured to seal directly against the rigid layer through a first gap in the first adhesive layer in response to pressure from thermal expansion of a fluid heated within the microfluidic chamber.

2. The microfluidic chip of claim 1, further comprising a spacer layer disposed between the first layer and the second layer that forms at least a portion of a wall of the microfluidic chamber.

3. The microfluidic chip of claim 2, wherein the wall has a smoothly curved ellipsoid geometry.

4. The microfluidic chip of claim 1, wherein size of the first void accommodates a fluid transfer instrument usable to inject the fluid on which the microfluidic reaction is performed into the microfluidic chamber through the first port.

5. The microfluidic chip of claim 1, further comprising:
   a second port connecting the exterior of the microfluidic chip to the microfluidic chamber through at least the rigid layer, the first polymer layer, and the first adhesive layer;
   a second self-sealing valve formed in the first polymer layer and disposed within the second port, the first self-sealing valve configured to seal directly against the rigid layer through a second gap in the first adhesive layer in response to pressure from thermal expansion of the fluid within the microfluidic chamber.

6. The microfluidic chip of claim 5, wherein air is ejected from the second self-sealing valve when the fluid is injected into the first port.

7. The microfluidic chip of claim 2, wherein the microfluidic chip comprises a plurality of layers formed and laminated using PCB techniques, the plurality of layers including the rigid layer, the first polymer layer, the first adhesive layer, the spacer layer, and the second polymer layer.

8. The microfluidic chip of claim 1, further comprising a first conductive layer comprising a single layer formed using PCB techniques, the first conductive layer comprising:
   a first heater element positioned to heat the fluid contained within the microfluidic chamber;
   a chip-portion of a drive circuit that is completed when the microfluidic chip is coupled with a controller of an apparatus; and
   a chip-portion of a voltage sensing circuit that is completed when the microfluidic chip is coupled with the controller;
   wherein the apparatus controls the first heater element using the drive circuit based on temperature calculations determined using the voltage sensing circuit.

9. A microfluidic chip for performing a microfluidic reaction comprising:
   a rigid layer;
   a first polymer layer that forms a first surface of a microfluidic chamber within the microfluidic chip;
   a first adhesive layer disposed between the rigid layer and the first polymer layer;
   a second polymer layer that forms a second surface of the microfluidic chamber;
   the microfluidic chip comprising a first port connecting an exterior of the microfluidic chip to the microfluidic chamber through at least the rigid layer, the first polymer layer, and the first adhesive layer;
   a first self-sealing valve formed in the first polymer layer and disposed within the first port, the first self-sealing valve configured to seal directly against the rigid layer through a first gap in the first adhesive layer in response to pressure from thermal expansion of a fluid within the microfluidic chamber; and
   a first conductive layer comprising a single layer formed using PCB techniques, the first conductive layer comprising:
      a first heater element positioned to heat the fluid contained within the microfluidic chamber,
      a chip-portion of a drive circuit that is completed when the microfluidic chip is coupled with a controller of an apparatus, and a chip-portion of a voltage sensing circuit that is completed when the microfluidic chip is coupled with the controller,
wherein the apparatus controls the first heater element using the drive circuit based on temperature calculations determined using the voltage sensing circuit.

* * * * *